United States Patent [19]

Lang, Jr. et al.

[11] Patent Number: 4,532,349

[45] Date of Patent: Jul. 30, 1985

[54] 2-AMINO-4'(PHENYLSULFONYL) ACETANILIDES

[75] Inventors: Stanley A. Lang, Jr., Blauvelt; Thomas L. Fields, Pearl River, both of N.Y.; Raymond G. Wilkinson, Montvale; Soon M. Kang, Dumont, both of N.J.; Yang-I Lin, Nanuet, N.Y.

[73] Assignee: American Cyanamid Company, Stamford, Conn.

[21] Appl. No.: 500,715

[22] Filed: Jun. 3, 1983

Related U.S. Application Data

[63] Continuation-in-part of Ser. No. 411,399, Aug. 25, 1982, abandoned.

[51] Int. Cl.³ .......................................... C07D 103/183

[52] U.S. Cl. ........................... 564/194; 260/453 AR; 548/252; 514/885; 564/212; 564/219; 564/220; 564/221

[58] Field of Search ................... 548/252; 260/465 E; 564/194

[56] References Cited

U.S. PATENT DOCUMENTS 2,948,736  8/1960  Martin ................................. 549/194

Primary Examiner—Glennon H. Hollrah
Assistant Examiner—D. B. Springer
Attorney, Agent, or Firm—Edward A. Conroy, Jr.

[57] ABSTRACT

A method of modulating the immune response system in a warm-blooded animal by the administration of N-substituted-phenylthioanilines, N-substituted-phenylsulfinylanilines, and N-substituted-phenylsulfonylanilines, certain of which are new compounds.

4 Claims, No Drawings

2-AMINO-4'(PHENYLSULFONYL) ACETANILIDES

CROSS REFERENCE TO RELATED APPLICATION

This application is a continuation-in-part of our abandoned application Ser. No. 411,399, filed Aug. 25, 1982.

DESCRIPTION OF THE INVENTION

This invention is concerned with a method of modulating the immune response system in a warm-blooded animal which comprises administering to said animal an effective amount of a compound of the formula:

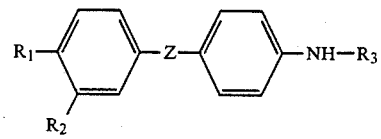

wherein $R_1$ is selected form the group consisting of hydrogen, fluoro, chloro, bromo, nitro, alkoxy having up to 3 carbon atoms and $-NHCOCH_2NHCH_3$; $R_2$ is hydrogen or chloro; and $R_3$ is selected from the group consisting of $-CH_2CN$, $-COCH_2NH_2$, $-COCH_2NHCH_3$, $-COCH_2Cl$, $-COCH_2CH_2Cl$,

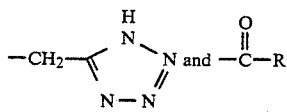

wherein R is alkyl having up to 4 carbon atoms such as methyl, isopropropyl, n-butyl, tert-butyl, etc.; and Z is thio (—S—), sulfinyl (—SO—) or sulfonyl (—SO$_2$—); with the proviso that at least one of $R_1$ and $R_2$ must be hydrogen but $R_1$ and $R_2$ may not both be hydrogen; together with the pharmaceutically acceptable salts thereof; in association with a pharmaceutically acceptable carrier.

In addition this invention is concerned with novel compounds of the formula:

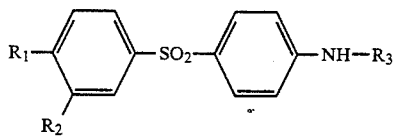

wherein $R_1$ is hydrogen, fluoro, chloro, or bromo and $R_2$ is hydrogen or chloro with the proviso that at least one of $R_1$ and $R_2$ must be hydrogen but $R_1$ and $R_2$ may not both be hydrogen; and $R_3$ is selected from the group consisting of $-COCH_2NH_2$,

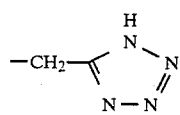

and $-CH_2CN$ together within their pharmaceutically acceptable salts.

The compounds of this invention may be prepared in accordance with the following reaction scheme:

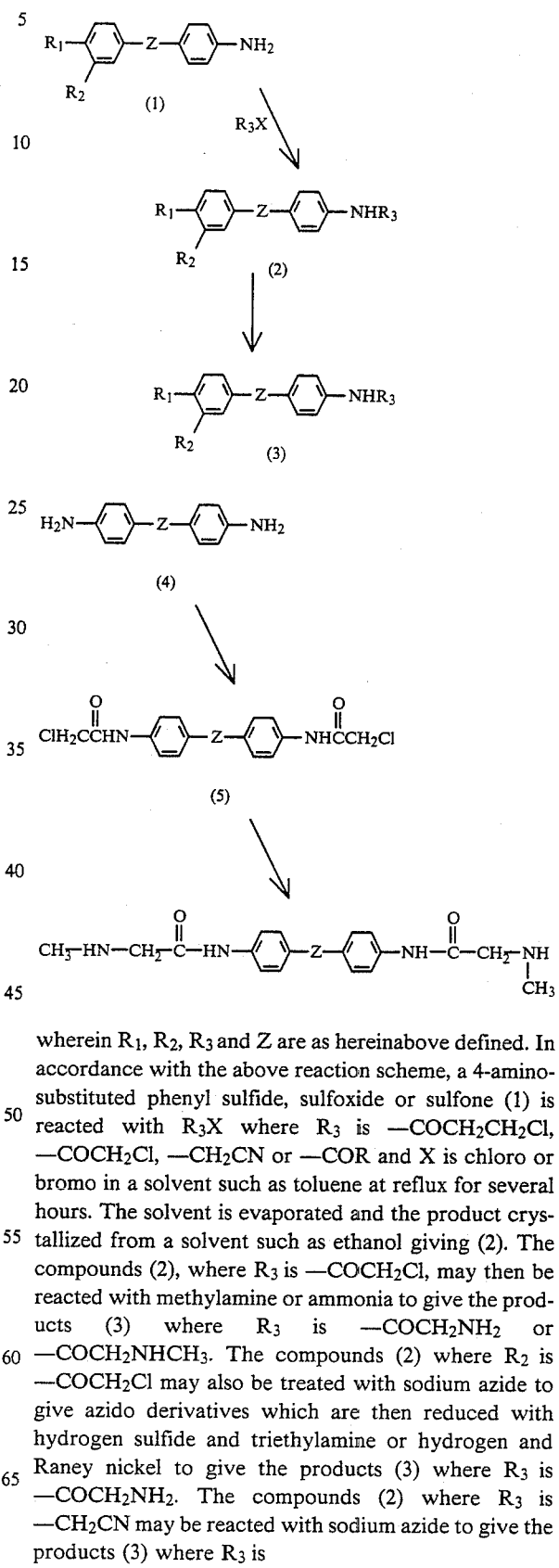

wherein $R_1$, $R_2$, $R_3$ and Z are as hereinabove defined. In accordance with the above reaction scheme, a 4-amino-substituted phenyl sulfide, sulfoxide or sulfone (1) is reacted with $R_3X$ where $R_3$ is $-COCH_2CH_2Cl$, $-COCH_2Cl$, $-CH_2CN$ or $-COR$ and X is chloro or bromo in a solvent such as toluene at reflux for several hours. The solvent is evaporated and the product crystallized from a solvent such as ethanol giving (2). The compounds (2), where $R_3$ is $-COCH_2Cl$, may then be reacted with methylamine or ammonia to give the products (3) where $R_3$ is $-COCH_2NH_2$ or $-COCH_2NHCH_3$. The compounds (2) where $R_2$ is $-COCH_2Cl$ may also be treated with sodium azide to give azido derivatives which are then reduced with hydrogen sulfide and triethylamine or hydrogen and Raney nickel to give the products (3) where $R_3$ is $-COCH_2NH_2$. The compounds (2) where $R_3$ is $-CH_2CN$ may be reacted with sodium azide to give the products (3) where $R_3$ is

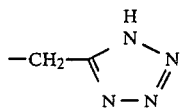

A bis(p-aminophenyl)sulfide, sulfoxide or sulfone (4) where Z is —S—, —SO— or —SO$_2$— is reacted with chloroacetyl chloride to give a bis[p-chloroacetamido)phenyl]sulfide or sulfoxide or sulfone (5) which is then reacted with methylamine in ethanol at reflux for several hours giving (6) where Z is as described above.

The use of immunomodulants and chemotherapeutic adjuvants constitutes a new therapeutic approach to the treatment of immune deficiencies and cancer and is based on the concept that there are distinctive antigens in or on most tumor cells (embryonal or transplantation antigens), that distinguish them from normal host cells. A majority of tumor immmunologists favor the view that potentially malignant cells constantly arise but because of their "foreigness" they are normally eliminated by a competent humoral and cellular immune system. Occasionally however, tumor cells escape this immune surveillance and continue to reproduce and cancer results. The reason for the failure of the normally efficient immune surveillance mechanisms are not fully understood but it is thought that the immune system becomes less effective with increasing age. It is depressed in certain genetic immuno-deficiency diseases, in various bacterial, fungal or viral infections, and in patients undergoing immuno-suppressive therapy. The growth of the neoplasm itself, as well as the various therapeutic modalities designed to treat the disease, e.g., cytotoxic chemotherapy and radiation, leads to a still greater depression of host resistance and results in an increased susceptibility to both exogenous and endogenous infections and perhaps accounts for the re-initiation of tumor growth and metastasis which frequently follows treatment-induced tumor remission.

If depression of the immune system can result in the growth of malignancies, regulation of any facet of the immune response may help the host to eliminate residual cancer cells. Therefore, it is desirable to search for chemical agents (i.e., immunoregulants) capable of restoring and stimulating host immune defense mechanisms in order to overcome the deficiencies which account for susceptibility to disease and failure to eradicate the cancer. Such immuno-regulating agents would likely be incapable of arresting the growth of a large tumor but their clinical utility would derive from their capacity to enhance normal immune surveillance mechanisms in patients whose tumor burden has been reduced by surgical, radiotherapeutic or chemotherapeutic methods.

Experimental studies in animals have demonstrated the antitumor potential of a number of immunoregulants including live organisms of bacillus Calmett-Guerin (BCG), heat-killed cells of Corynebacterium parvum, polynucleotides, and the anthelmintic drug, levamisole. These substances have been shown to stimulate cellular immunity and to produce tumor regression. Some successes have been claimed in early clinical trials with BCG against malignant melanoma and acute leukemia, and with levamisole against lung cancer and breast cancer. Although the antitumor effects produced by these agents have been promising, significant therapeutic benefits have yet to be realized. Since this is a new therapeutic approach, new drug and methods of treatments must receive careful clinical evaluation in order to reveal their full potential.

Modern research is directed to the discovery of a drug similar to, but more potent than, known immunoregulants such as levamisole that would be effective in the eradication of tumor cells when used in conjunction with standard therapeutic measures. Stimulators of host resistance may be detected in animal models that can, in fact, detect both immunostimulators and anticancer agents. Mice are put in a condition simulating immunodepression common to cancer patients. This is accomplished by infeting mice with a leukemia virus which produces both leukemia and a disease-related immunodepression. Effective drugs are recognized by their ability to restore or enhance the antibody response in the experimental mice, or to inhibit tumor progression.

The active compounds and novel compositions of the present invention are active as immunomodulators when tested according to the following procedures:

Restoration of Antibody formation in Mice with Rauscher Virus-Induced Leukemia

Infection of Balb/c mice with Rauscher leukemia virus (RLV) is characterized by: (1) a rapidly developing veremia, (2) suppression of the primary antibody response to antigens administered a few days after virus infection, (3) a progressive enlargement of the spleen (splenomegaly), and (4) death resulting from splenic rupture and hemorrhage. The protocol used to infect Balb/c mice with RLV and to test drugs for anticancer and/or immunostimulating activity is as follows:

Day 0: Inject 0.2 ml. of a 20% (w/v) RLV-infected spleen cell extract intraperitoneally (IP) into groups of 5 Balb/c mice. The spleen cell extract is prepared from mice infected with RLV 21 days previously.

Day +6, +7, +8: Test compounds are administered orally or by IP injection, in 0.5 ml. of normal saline containing 0.2% Noble agar.

Day +7: Inject 0.5 ml. IP of a thrice saline washed 10% suspension of sheep red blood cells (S-RBC).

Day +14: Bleed mice from the retro-orbital sinus; pool blood from each group. Serum, harvested from pooled blood of each group of mice is stored at 4° C. for 24 hours. Hemagglutinin tests are performed by standard procedures using a microtiter technique. Acceptable hemagglutinin titer for leukemic (immunosuppressed) mice is ≦1:128. The positive control compounds are Poly I:C (polyinosinic acid:polycytidylic acid) and Sarcosine administered intraperitoneally on days +6, +7, and +8. Acceptable positive control hemagglutinin titers are 4-fold higher than the titers obtained in leukemic control mice.

Typical compounds of this invention are active in this test, in that they produce a 4-fold or higher increase in hemagglutinin titer to sheep-RBC's, relative to the placebo treated, RLV-infected control mice. Results of this test appear in Table I.

TABLE I

Antibody Restoration in Mice with Rauscher Virus-Induced Leukemia

| Compound | Dose(mg/kg) | Route | Fold increase in Serum Hemagglutinin Titer |
| --- | --- | --- | --- |
| 3-chloro-4'-(p-nitrophenylthio)-propionaldehyde | 1800 | oral | 64 |
| 2-methylamino-4'-(p-nitrophenylthio)-acetanilide, hydrochloride | 200 | oral | 8 |
| 2-chloro-4'-(m-chlorophenylsulfonyl)-acetanilide | 1800 | oral | 8 |
| 2-amino-4'-(m-chlorophenylsulfonyl)-acetanilide | 400 | oral | 16 |
| 4'-(m-chlorophenylsulfonyl)-2-methylamino-acetanilide | 800 | oral | 4 |
| 4',4'''-sulfonylbis(2-methylamino-acetanilide | 1800 | oral | 8 |
| 4'-(p-chlorophenylsulfonyl)acetanilide | 100 | oral | 16 |
| 2-amino-4'-(p-chlorophenylsulfonyl)acetanilide hydrochloride | 100 | oral | 4 |
| [p-(p-chlorophenylsulfonyl)anilino]acetonitrile | 400 | oral | 32 |
| 5-[[p-(p-chlorophenylsulfonyl)anilino]methyl]-1H—tetrazole | 400 | oral | 8 |
| 2-amino-N—[4-[(4-fluorophenyl)sulfonyl]phenyl]acetamide | 300 | oral | 16 |
| N—[4-[(-fluorophenyl)sulfonyl]phenyl]acetamide | 400 | oral | 64 |
| N—[4-[(4-bromophenyl)sulfonyl]phenyl]acetamide | 200 | oral | 16 |
| N—[4-[(3-chlorophenyl)sulfonyl]phenyl]acetamide | 100 | IP | 4 |
| N—[4-[(4-fluorophenyl)sulfinyl]-phenyl]acetamide | 100 | IP | 4x |
| N—[4-[(4-methoxyphenyl)thio]phenyl]-acetamide | 400 | Oral | 4x |
| N—[4-[(4-methoxyphenyl)sulfinyl]-phenyl]acetamide | 400 | Oral | 4x |
| N—[4-[(4-chlorophenyl)sulfinyl]-phenyl]acetamide | 100 | IP | 4x |
| N—[4-[(4-chlorophenyl)thio]phenyl]-acetamide | 100 | IP | 16x |
| N—[4-[(4-bromophenyl)thio]phenyl]-acetamide | 100 | IP | 8x |
|  | 200 | Oral | 16x |
| N—4-[(4-bromophenylsulfinyl]phenyl]-acetamide | 400 | Oral | 8x |
| N—[4-[(4-fluorophenyl)sulfonyl]phenyl]-2-methylpropanamide | 200 | Oral | 16x |

The compounds of the present invention are effective as immunomodulators (that is, they modulate the immuneresponse) when administered orally in amounts ranging from about 5 mg. to about 400 mg. per kilogram of body weight per day. A preferred dosage regimen for optimum results would be from about 5 mg. to about 50 mg. per kilogram of body weight per day, and such dosage units are employed that a total of from about 350 mg. to about 3.5 grams of the active compound for a subject of about 70 kg. of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A practical advantage of this invention is that the active compounds may be administered in any convenient manner such as the oral or buccal routes.

The compounds of the present invention may be orally administered, for example, with an inert diluent or with an assimilable edible carrier, or they may be enclosed in hard or soft shell gelatin capsules, or they may be compressed into tablets. For oral therapeutic administration, the active compounds may be incorporated with excipients and used in the form of tablets, troches, capsules, elixirs, suspensions, syrups, wafers, and the like. Such compositions and preparations should contain at least 0.5% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound. The tablets, troches, pills, capsules and the like may also contain the following: a binder such as gum tragacanth, acacia, corn starch or gelatin; excipients such as dicalcium phosphate; disintegrating agents such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The invention will be described in greater detail in conjunction with the following specific examples.

EXAMPLE 1

2-Chloro-4'-(p-nitrophenylthio)acetanilide

A mixture of 10.0 g or 4-amino-4'-nitrophenylsulfide and 4.5 g of chloroacetyl chloride in 150 ml of toluene was refluxed for 48 hours. The solvent was removed by evaporation and the residue crystallized from ethanol, giving 12 g of the desired product, mp 217°–219° C.

EXAMPLE 2

3-Chloro-4'(p-nitropenylthio)propionamilide

To a mixture of 5.0 g of 4-amino-4'-nitrodiphenylsulfide in 120 ml of toluene and 20 ml of dichloromethane was added to 2.6 g of 3-chloropropionyl chloride in 15 ml of toluene, dropwise. The mixture was heated and stirred at reflux for 2 hours then the solvent was evaporated and the residue recrystallized from ethanol, giving 6.2 g of the desired product, mp 145°–147° C.

EXAMPLE 3

2-Methylamino-4'-(p-nitrophenylthio)acetanilide hydrochloride

A mixture of 3.0 g of 2-chloro-4'-(p-nitrophenylthio)acetanilide and a 4.0% aqueous solution of methylamine in ethanol was refluxed for 4 hours. The solvent was evaporated, the residue dissolved on dichloromethane and crystallized by the addition of hexane, giving 2.25 g of the desired product, mp 86°–89° C.

EXAMPLE 4

2-Chloro-4'-m-chlorophenylsulfonyl)acetanilide

To a stirred mixture of 28.8 g of 3-chlorothiophenol and 23.3 g of sodium carbonate in 250 ml of water was added 31.5 g of 4-chloro nitrobenzene followed by 200 ml of ethanol. The mixture was stirred at reflux for 4 hours and then filtered. The solid was treated with dichloromethane and water and then recrystallized from toluene, giving 42.1 g of 3-chlorophenyl-4'-nitrophenylsulfide.

A mixture of 40.0 g of 3-chlorophenyl-4'-nitrophenylsulfide, 0.7 ml of 30% hydrogen peroxide and 230 ml of glacial acetic was hydrogenated in a Parr apparatus for 1.5 hours. The reaction mixture was filtered and the solid washed with two 150 ml portions of dioxane. Evaporation of the filtrate and wash gave a residue which was crystallized from ethanol, giving 43.4 g of 3-chlorophenyl-4'-nitrophenylsulfone.

A 12.5 g portion of 3-chlorophenyl-4'-nitrophenylsulfone in dioxane was hydrogenated in a Parr apparatus with Raney nickel catalyst, giving 4.9 g of 3-chlorophenyl-4'-aminophenylsulfone.

To a solution of 2.57 g of 3-chlorophenyl4'-aminophenylsulfone and 3.0 ml of 2-methoxyethylether in 0.5 ml of dioxane was added 0.5 ml of chloroacetylchloride. The mixture was heated at 90°–110° C. for one hour. The solvent was evaporated and the residue recrystallized from cold hexane, than ethanol, giving 1.3 g of the desired product, mp 130°–132° C.

EXAMPLE 5

2-Amino-4'-(m-chlorophenylsulfonyl)acetanilide

A mixture of 2.0 g of 2-chloro-4'-(m-chlorophenylsulfonyl)acetanilide, 0.41 g of sodium azide, 20 ml of water and 40 ml of ethanol was refluxed for 3.5 hours and then evaporated to dryness. The residue was crystallized from ethanol, giving 1.2 g of 2-azido-4'-(m-chlorophenylsulfonyl)acetanilide, mp 125°–126° C.

A mixture of 12 g of 2-azido-4'-(m-chlorophenylsulfonyl)acetanilide and 8 ml of Raney nickel in 150 ml of p-dioxane and 50 ml of ethanol was hydrogenated in a Parr shaker with an initial pressure of 30 psi of hydrogen for 2 hours. The mixture was filtered through a celite pad and the volatiles removed from the filtrate. The residue was crystallized from p-dioxane, giving 6.2 g of the desired product, mp 195°–196° C.

EXAMPLE 6

4'-(m-Chlorophenylsulfonyl)-2-methylamino-acetanilide

A mixture of 6.0 g of 3-chlorophenyl-4'-(m-chlorophenylsulfonyl)acetanilide, 1100 ml of methylamine and 20 ml of ethanol was refluxed for 3.5 hours. The solvent was evaporated and the residue partitioned between dichloromethane and water. The dichloromethane portion was evaporated and the residue crystallized from ethanol giving 2.48 g of the desired product, mp 110°–112° C.

EXAMPLE 7

4'4'''-Sulfonybis(2-methylaminoacetanilide)

To a stirred solution of 24.83 g of bis(p-aminophenyl)-sulfone in 100 ml of dioxane and 200 ml of dimethoxyethyl ether at 50° C. was added a 1:1 mixture of chloroacetyl chloride and dimethoxyenthyl ether. The mixture was heated at 90° C. for 3.5 hours and then allowed to stand at ambient temperature. The solid was collected and crystallized giving 10.2 g of bis[(p-chloroacetamido)phenyl]sulfone.

A mixture of 5.0 g of bis-[(p-chloroacetamido)-phenyl]sulfone and 100 ml of methylamine in 100 ml of ethanol was refluxed for 3 hours. The solvent was evaporated and the residue recrystallized from ethanol, giving 2.8 g of the desired product, mp 166°–168° C.

EXAMPLE 8

4'-(p-chlorophenylsulfonyl)acetanilide

A mixture of 70.1 g of N-acetylsulfanilyl chloride and 60 g of aluminum chloride in 200 ml of p-chlorobenzene was heated until the evolution of hydrogen chloride ceased and then refluxed for 2 hours. The chlorobenzene was removed by decantation and the residue diluted with ether. The resulting gummy solid was recovered by filtration and treated with dilute hydrochloric acid and ethanol. The resulting solid was collected, dissolved in hot ethanol and concentrated, giving 19.31 g of the desired product as pale gray crystals, mp 187.5°–188.5° C.

EXAMPLE 9

2-Amino-4'-(p-chlorophenylsulfonyl)acetanilide hydrochloride

A mixture of 5.14 g of 4'-(p-chlorophenylsulfonyl)acetanilide, 1.42 g of chloroacetyl chloride, 26 ml of p-dioxane and 14 ml of methoxyethyl ether was heated with stirring at 90°–100° C. for 2½ hours, then worked up, giving 7.9 g of 2-chloro-4'[p-(p-chlorophenylsulfonyl)phenyl]acetanilide.

A mixture of 6.0 g of the above compound and 120 ml of liquid ammonia was heated at 140° C. in a sealed bomb for several hours, then opened and allowed to stand overnight. The mixture was treated with acetone, filtered, evaporated and crystallized from hexane with refrigeration. Further recrystallization gave 1.8 g of the desired product after conversion to the hydrochloride salt, mp 143°–145° C.

EXAMPLE 10

[p-(p-chlorophenylsulfonyl)anilino]acetonitrile

A mixture of 43.5 g of p-chlorothiophenol, 47.1 g of p-chloronitrobenzene, 39.0 g of sodium carbonate, 120 ml of water and 150 ml of ethanol was heated at 100° C. for 19 hours, giving 80.0 g of 4-chloro4'-nitrodiphenylsulfide, which was then dissolved in a mixture of 400 ml of acetic acid and 100 ml of 30% hydrogen peroxide and stirred at 100° C. for one hour, giving 80.2 g of the corresponding sulfonyl derivative.

The sulfonyl derivative was catalytically hydrogenated to the corresponding amino derivative.

A 16.1 g portion of the amino derivative, 4.98 g of bromoacetonitrile, 9.0 g of sodium bicarbonate and 18 ml of 1-methyl-2-pyrrolidinone was mixed, stirred at 106° C. under nitrogen for 3 hours and then quenched with ice water giving 11.8 g of the desired product as tan crystals, mp 130°–132° C.

EXAMPLE 11

5-[[p-(p-chlorophenylsulfonyl)anilino]methyl]-1H-tetrazole

A reaction mixture comprising 6.14 g of [p-(p-chlorophenylsulfonyl)anilino]acetonitrile, 1.43 g of sodium azide, 30 mg of lithium chloride, 1.18 g of ammonium chloride and 10 ml of dimethylformamide was stirred at 90° C. for 34 hours and then filtered. The solvent was removed in vacuo, the residue suspended in 50 ml of water and acidified with hydrochloric acid to $pH_2$. The resulting solid was collected and recrystallized from acetic acid, giving 5.4 g of the desired product as tan crystals, mp 102°–105° C.

EXAMPLE 12

2-Amino-N-[4-[(4-fluorophenyl)sulfonyl]phenyl]acetamide

4-Amino-4'-fluorodiphenylsulfone was prepared from p-fluorothiophenol and p-chloronitrobenzene by converting the sulfide to the sulfone and reducing the nitro substituent to the amino derivative by the procedures giving in Example 10. A 15.0 g portion of the sulfone was then stirred in 200 ml of dichloromethane in an ice bath and 9.18 ml of triethylamine were added. A solution of 5.26 ml of chloroacetyl chloride in 50 ml of dichloromethane was added at such a rate as to maintain the temperature below 25° C. The ice bath was removed, the mixture stirred for one hour at room temperature then washed twice with saturated sodium bicarbonate solution, twice with water, treated with charcoal, dried and concentrated to a solid, giving 13.7 g of 4-fluoro-4'-chloroacetamidodiphenylsulfone.

An 11.0 g portion of this solid was combined with 2.4 g of sodium azide in 50 ml of dimethylsulfoxide, stirred overnight, poured into 500 ml of ice and water and the solid collected. This solid was recrystallized from 150 ml of toluene, giving 9.8 g of 2-azido-N-[4-[(4-fluorophenyl)sulfonyl]phenyl]acetamide.

A 2.0 g portion of this azide was dissolved in 40 ml of p-dioxane and subjected to hydrogenation with Raney nickel catalyst for 1.5 hours. The mixture was filtered, the filtrate concentrated to a residue and recrystallized from ethanol giving 944 mg of the desired product as white crystals, mp 181°–184° C.

EXAMPLE 13

N[4-[(4-fluorophenyl)sulfonyl]phenyl]acetamide

A 2.51 g portion of 4-amino-4'-flourodiphenylsulfone was slurried in 100 ml of dichloromethane. A 1.84 ml portion of triethylamine was added and the mixture was cooled in an ice bath. A 1.05 ml portion of acetyl chloride in 60 ml of dichloromethane was added dropwise over 15 minutes, the ice bath was removed and the mixture stirred at room temperature for 48 hours. The solution was washed successively with water, sodium bicarbonate solution, water and sodium chloride solution then dried and concentrated to a solid. The solid was recrystallized from 125 ml of toluene, giving 1.6 g of the desired product as white crystals, mp 181°–183° C.

EXAMPLE 14

N-[4-[(4-Bromophenyl)sulfonyl]phenyl]acetamide

A mixture of 28.35 g of 4-bromothiophenol, 23.55 g of 4-chloronitrobenzene, 19 g of sodium carbonate, 100 ml of ethanol and 75 ml of water was heated at 100° C. for 4 hours, then diluted with 500 ml of water. The resulting yellow solid was collected, slurried in a mixture of 250 ml of acetic acid and 100 ml of water, heated at 100° C. for 2 hours cooled and diluted with 500 ml of water. The white crystals were collected, giving 46.0 g of 4-bromo-4'-nitrodiphenylsulfone.

A 37.6 g portion of the above nitro derivative was reduced to the corresponding amino derivative.

A 3.11 g portion of the above amino derivative was slurried in 75 ml of dichloromethane, 2.15 ml of triethylamine was added and the mixture was cooled in an ice bath. A 1.13 ml portion of acetylchloride in 40 ml of dichloromethane was added dropwise over 30 minutes the ice bath was removed and the mixture was stirred over 48 hours. The solution was worked up as described in Example 13, giving 2.5 g of the desired product as tan crystals, mp 195°–199° C.

EXAMPLE 15

N-[4-[(3-chlorophenyl)sulfonyl]phenyl]acetamide

To a cooled solution of 3.0 g of 3-chlorophenyl-4'-aminophenylsulfone in 60 ml of dichloromethane was add simultaneously, dropwise 0.92 ml of acetylchloride and 1.72 ml of triethylamine over a 10 minute period. The reaction was stirred at room temperature for 2 hours, then allowed to stand overnight and poured into 60 ml of water. The organic layer was separated and evaporated to a residue. The residue was crystallized from toluene, giving 3.2 g of the desired product, mp 149°–150° C.

EXAMPLE 16

N-[4-[(4-Fluorophenyl)thio]phenyl]acetamide

4-Fluoro-4'-nitrodiphenylsulfide was hydrogenated in p-dioxane, using Raney nickel catalyst, giving 4-[(4-fluorophenyl)thio]-benzeneamine.

A 2.19 g portion of this amine was dissolved in 50 ml of dichloromethane, cooled in an ice bath and treated with 1.52 g of triethylamine. The mixture was then treated dropwise with a solution of 1.18 g of acetyl chloride in 20 ml of dichloromethane over 20 minutes. This mixture was stirred at room temperature overnight, then the solution was washed successively with water, saturated aqueous sodium bicarbonate, water and brine, dried over magnesium sulfate, filtered and concentrated to dryness. The residue was recrystallized from methanol-water, giving 2.26 g of the desired product as colorless crystals, mp 140°–141° C.

EXAMPLE 17

N-[4-[4(-Fluorophenyl)sulfinyl]phenyl]acetamide

A solution of 1.3 g of N-[4-[(4-fluorophenyl)thio]phenyl]actamide in 75 ml of glacial acetic acid was heated to 50°–70° C., treated with 0.17 g of 30% hydrogen peroxide and stirred for one hour. The mixture was diluted with 5 volumes of ice water and stirred. The solid was collected, washed with water and dried, giving 1.2 g of the desired product as a colorless solid, mp 169°–170° C.

EXAMPLE 18

N-[4-[(4-Methoxyphenyl)thio]phenyl]-acetamide

4-Methoxy-4'-nitrodiphenylsulfide was reduced to 4-[(4-methoxyphenyl)thio]-benzeneamine as described in Example 16 and then further reacted as described in Example 16, giving the desired product as a pale yellow solid, mp 100°–102° C.

EXAMPLE 19

N-[4-[(4-Methoxyphenyl)sulfinyl]phenyl]-acetamide

An 8.2 g portion of N-[4-[(4-methoxyphenyl)thio]phenyl]acetamide was reacted as described in Example 17, giving 6.7 g of the desired product as a pale yellow solid, mp 63°–65° C.

EXAMPLE 20

N-[4-[(4-Chlorophenyl)thio]phenyl]-acetamide

4-Chloro-4'-nitrodiphenylsulfide was reduced to 4-[(4-chlorophenyl)thio]-benzeneamine and then further reacted as described in Example 16, giving the desired product as beige crystals, mp 140°–141° C.

EXAMPLE 21

N-[4-[(4-Chlorophenyl)sulfinyl]phenyl]-acetamide

An 8 g portion of N-[4-[(4-chlorophenyl)thio]phenyl]-acetamide was reacted as described in Example 17, giving 7 g of the desired product as a colorless solid, mp 160°–162° C.

EXAMPLE 22

N-[4-[(4-Bromophenyl)thio]phenyl]-acetamide

4-Bromo-4'-nitrodiphenylsulfide was reduced to 4-[(4-bromophenyl)thio]-benzeneamine and further reacted as described in Example 16, giving the desired product as beige crystals, mp 153°–155° C.

EXAMPLE 23

N-[4-[(4-Bromophenyl)sulfinyl]phenyl]-acetamide

A 10 g portion of N-[4-[(4-bromophenyl)thio]phenyl]-acetamide was reacted as described in Example 17, giving 2.31 g of the desired product as beige crystals, mp 190°–191° C.

EXAMPLE 24

N-[4-[(4-Fluorophenyl)sulfonyl]phenyl]-2-methylpropanamide

A 2.51 g portion of 4-[4-fluorophenyl)sulfonyl]benzeneamine was reacted as described in Example 16, using propionyl chloride in place of acetyl chloride giving 2.74 g of the desired product, mp 112°–115° C.

EXAMPLE 25

N-[4-(Phenylthio)-phenyl]-acetamide

4-Nitrodiphenyl sulfide was reduced to 4-(phenylthio)-benzeneamine and further reacted as described in Example 16, giving the desired product as orange crystals, mp 142°–144° C.

EXAMPLE 26

N-[4-(Phenylsulfinyl)phenyl]-acetamide

A 2.43 g portion of N-[4-(phenylthio)phenyl]acetamide was reacted as described in Example 17, giving 1.1 g of desired compound as a colorless solid, mp 135°–137° C.

We claim:

1. A compound selected from the group consisting of those of the formula:

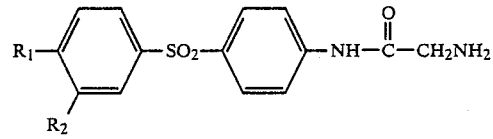

wherein $R_1$ is hydrogen, fluoro, chloro or bromo and $R_2$ is hydrogen or chloro with the proviso that at least one of $R_1$ and $R_2$ must be hydrogen but $R_1$ and $R_2$ may not both be hydrogen; and the pharmacologically acceptable acid-addition salts thereof.

2. The compound according to claim 1; 2-amino-4'-(m-chlorophenylsulfonyl)acetanilide.

3. The compound according to claim 1; 2-amino-4'-(p-chlorophenylsulfonyl)acetanilide hydrochloride.

4. The compound according to claim 1; 2-amino-4'-(p-fluorophenylsulfonyl)acetanilide.

* * * * *